(12) United States Patent
Jacquot et al.

(10) Patent No.: US 8,889,913 B2
(45) Date of Patent: Nov. 18, 2014

(54) HYDRIDE TRANSFER PROCESS FOR KETONE PREPARATION

(75) Inventors: Roland Jacquot, Francheville (FR); Philippe Marion, Vernaison (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/813,616

(22) PCT Filed: Jul. 20, 2011

(86) PCT No.: PCT/EP2011/062413
§ 371 (c)(1),
(2), (4) Date: Apr. 8, 2013

(87) PCT Pub. No.: WO2012/016831
PCT Pub. Date: Feb. 9, 2012

(65) Prior Publication Data
US 2013/0204046 A1  Aug. 8, 2013

(30) Foreign Application Priority Data

Aug. 4, 2010  (FR) ...................................... 10 56436

(51) Int. Cl.
*C07C 45/29* (2006.01)
*C07C 27/04* (2006.01)
*C07C 29/143* (2006.01)

(52) U.S. Cl.
CPC .................. *C07C 27/04* (2013.01); *C07C 45/29* (2013.01); *C07C 29/143* (2013.01); *C07C 2101/14* (2013.01)
USPC ............................. 568/347; 568/376; 568/880

(58) Field of Classification Search
USPC ......................................... 568/347, 376, 880
See application file for complete search history.

(56) References Cited

U.S. PATENT DOCUMENTS 6,340,775 B1  1/2002  Jacquot et al.

FOREIGN PATENT DOCUMENTS

EP  0 603 409 A1  6/1994
WO  98/30517 A1  7/1998

OTHER PUBLICATIONS

Creyghton et al, "Stereoselective Meerwein—Ponndorf—Verley and Oppenauer reactions catalysed by zeolite BEA," Journal of Molecular Catalysis A: Chemical, 1997, pp. 457-472, vol. 115.
Kabo et al, "Thermodynamic properties of cyclohexanol and cyclohexanone," J. Chem. Thermodyn., 1988, pp. 429-437, vol. 20.
Kuno et al, "Oxidation of Alcohols to Aldehydes and Ketones over Hydrous Zirconium(IV) Oxide Modified by Trimethylsilyl Chloride," Bull. Chem. Soc. Jpn., 1993, pp. 1699-1702, vol. 66.
Kuno et al, "Oxidation of Secondary Alcohols over Hydrous Zirconium(IV) Oxide," Bull. Chem. Soc. Jpn., 1990, pp. 1943-1946, vol. 63.
Leyrit et al, "A novel heterogeneous molecular catalyst for the Meerwein—Ponndorf—Verley and Oppenauer reactions," Journal of Molecular Catalysis A: Chemical, 1996, pp. 395-400, vol. 112.
Raja et al, "Calcined Layered Double Hydroxides as Basic Heterogeneous Catalysts for the Oppenauer Oxidation of Alcohols," Bull. Chem. Soc. Jpn., 1999, pp. 2117-2119, vol. 72.
International Search Report issued on Sep. 23, 2011, by the European Patent Office as the International Searching Authority in International Patent Application No. PCT/EP2011/062413.
Written Opinion of the International Searching Authority issued on Feb. 5, 2013, in International Patent Application No. PCT/EP2011/062413.

*Primary Examiner* — Sikarl Witherspoon
(74) *Attorney, Agent, or Firm* — Dentons US LLP

(57) ABSTRACT

A hydride transfer process within a reaction between an alcohol and a ketone and in the presence of a heterogeneous catalyst is described. The process can transfer a hydride from an alcohol to a ketone, thus enabling reduction of the ketone and oxidation of the alcohol. Further described, is a process for the simultaneous preparation of cyclohexanone and isopropanol enabling an optimized industrial operation. A mixture of compounds useful for implementing the process and comprising two different ketones and two different alcohols is also described.

5 Claims, No Drawings

HYDRIDE TRANSFER PROCESS FOR KETONE PREPARATION

CROSS-REFERENCE TO PRIOR APPLICATIONS

This application is a National Stage of PCT/EP2011/062413, filed Jul. 20, 2011, and designating the United States (published in French on Feb. 9, 2012, as WO 2012/016831 A1), which claims priority to FR 10/56436, filed Aug. 4, 2010, each hereby expressly incorporated by reference in its entirety and each assigned to the assignee hereof.

The present invention relates to a hydride transfer process within a reaction between an alcohol and a ketone and in the presence of a heterogeneous catalyst. The simplified process according to the invention transfers a hydride from an alcohol to a ketone, thus simultaneously enabling the reduction of the ketone and the oxidation of the alcohol. In particular, the invention relates to a simplified process for the simultaneous preparation of cyclohexanone and isopropanol enabling an excellent, very significantly improved efficiency.

The invention also relates to a mixture of compounds useful for implementing the process according to the invention and comprising two different ketones and two different alcohols.

Cyclohexanone is an important reactant within the context of the preparation of adipic acid used for manufacturing polyamide, for example polyamide PA-6,6, or else polyurethanes. It is also an important intermediate in the preparation of caprolactam, a monomer used in the manufacture of polyamide PA-6.

The simultaneous preparation of an alcohol and acetone or 2-butanone from isopropanol or isobutanol and a ketone via the Meerwein-Ponndorf-Verley (MPV) reaction is known. The preparation of ketones and alcohols from an alcohol and a ketone via a reaction of Oppenauer type is known.

Usually, the objective of the reactions from the prior art is however preparation of alcohol by hydrogenation of the carbonyl derivative or of the corresponding unsaturated alcohol.

Thus, it is known how to manufacture cyclohexanol by hydrogenation of phenol, often at pressures between 10 and 50 bar. However, this reaction is carried out under conditions that are difficult, owing to the use of hydrogen, and expensive.

It is also known how to obtain cyclohexanone by dehydrogenation of cyclohexanol using copper-based catalysts, at a temperature between 250 and 300° C. This reaction is therefore a highly energy-consuming reaction and the handling of the hydrogen produced by the reaction is problematic.

It is also known how to produce cyclohexanol by oxidation of cyclohexane in air in the presence of chromium-based catalysts.

It is furthermore known how to prepare isopropanol by hydrogenation of acetone via chromium catalysis which also poses the problem of the handling of the hydrogen.

Thus, international patent application WO-98/30517 describes the reduction of a carbonyl compound by reaction with an alcohol in the presence of a catalyst, in particular, this document describes the reduction of 4-alkylcyclohexanones in the presence of isopropanol with a view to preparing the corresponding cyclohexane alcohols according to the following reaction scheme:

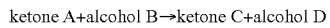

There is thus a need for a process that is simple to implement and that makes it possible to synthesize cyclohexanone while avoiding the mentioned drawbacks of known processes.

The present invention makes it possible, contrary to what was known from the prior art, to prepare ketones from alcohols via a hydride transfer process within a reaction between an alcohol and a ketone and in the presence of a heterogeneous catalyst, moreover under conditions that were hitherto reputed to be difficult or even impossible to implement. Indeed, it would have been expected that an excess of ketone would lead to a significant risk of parasitic chemical reactions; or else that the catalysts used would lead to reactions with the ketone produced.

The present invention thus proposes to provide a process that is simplified and that provides full or partial solutions to the problems and drawbacks of the prior art processes. Said process furthermore has certain other advantages such as the fact that the preparation of an alcohol, in particular isopropanol, permitted by the invention is in general the product of the hydrogenation of the corresponding ketone, in particular acetone. Advantageously, the process of the invention uses a reactant that may also be used as a solvent for the reaction. The process according to the invention also makes it possible to use one of the reactants as a hydride source or hydride acceptor.

One subject of the present invention is therefore to provide a process for preparing a ketone of formula (I) and an alcohol of formula (II):

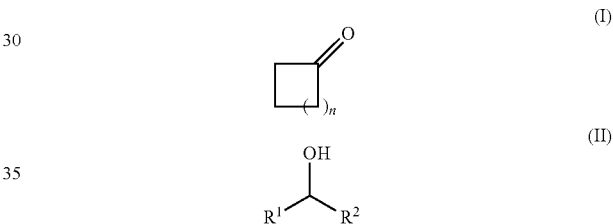

by transfer of a hydride, in the presence of a heterogeneous catalyst, between an alcohol of formula (III) and a ketone of formula (IV), present in a (III)/(IV), alcohol of formula (III)/ketone of formula (IV), molar ratio ranging from 1/10 to 2/1,

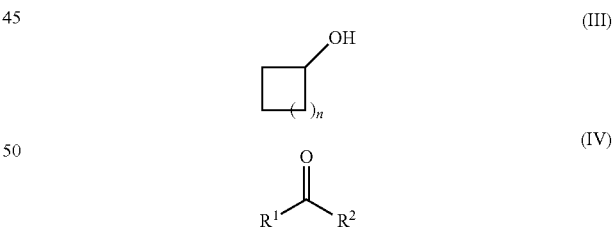

in which:
n represents an integer ranging from 1 to 9;
$R^1$ and $R^2$ independently represent a $C_1$-$C_{10}$ hydrocarbon-based group.

For the process according to the invention, n advantageously represents 2, 3, 4, 5 or 9, in particular 2, 3 or 9. Preferably, n represents 3.

Preferably, for the process according to the invention, $R^1$ or $R^2$ independently represent $CH_2R^3$, $CHR^4R^5$ or $CR^6R^7R^8$, in which:
$R^3$ represents a linear or branched $C_1$-$C_9$ alkyl;
$R^4$ and $R^5$ independently represent a linear or branched $C_1$-$C_8$ alkyl;

$R^6$, $R^7$, $R^8$ independently represent a linear or branched $C_1$-$C_6$ alkyl.

Most preferably, $R^1$ and $R^2$ independently represent methyl, ethyl, n-propyl, iso-propyl, t-butyl; most particularly, $R^1$ and $R^2$ represent methyl.

Thus, the ketone of formula (IV) is advantageously selected from low molecular weight ketones, in particular from ketones for which the molecular weight is less than 130 g/mol, or even less than 100 g/mol.

For the process according to the invention, the (III)/(IV) molar ratio is advantageously selected between 1/10 and 2/1, preferably between 1/8 and 1/2.

In accordance with the invention, said heterogeneous catalyst used in the preparation process according to the invention is selected from zeolites, hydroxyapatites with various Ca/P atomic ratios, tricalcium phosphate, magnesium phosphates, olivine, aluminas and rare-earth oxides, as they are or as a mixture with other oxides.

For the process according to the invention, the heterogeneous catalyst is generally a hydride transfer catalyst. As catalysts for the process according to the invention, mention may be made of zeolite catalysts or zeolite-based catalysts.

The term "zeolite" is understood to mean a crystallized tectosilicate of natural or synthetic origin, the crystals of which result from the three-dimensional assembly of tetrahedral $SiO_4$ and $TO_4$ units: T representing a trivalent element such as aluminium, gallium, boron or iron, preferably aluminium. Zeolites of aluminosilicate type are the most common.

Within the crystal lattice the zeolites have a system of cavities connected together by channels that have a well-defined diameter and that are referred to as pores. They may have a network of one-dimensional, two-dimensional or three-dimensional channels.

In the process of the invention, a natural or synthetic zeolite may be used. As examples of natural zeolites that can be used, mention may be made, for example, of: chabazite, clinoptilotite, erionite, phillipsite and offretite. As examples of synthetic zeolites having a one-dimensional network, mention may be made, inter alia, of zeolite ZSM-4, zeolite L, zeolite ZSM-12, zeolite ZSM-22, zeolite ZSM-23 and zeolite ZSM-48. As examples of zeolites having a two-dimensional network that are preferably used, mention may be made of mordenite and ferrierite. As regards zeolites having a three-dimensional network, mention may more particularly be made of zeolite β (BEA), titanium-containing zeolite β, tin-containing zeolite β (SnBEA), zeolite Y, zeolite X, zeolite ZSM-5, zeolite ZSM-11 and offretite. Preferably, use is made of synthetic zeolites, and more particularly of the zeolites that are in the following forms:

mazzite having an Si/Al molar ratio of 3.4;
zeolite L having an Si/Al molar ratio from 1.5 to 3.5;
mordenite having an Si/Al molar ratio from 5 to 15;
ferrierite having an Si/Al molar ratio from 3 to 10;
offretite having an Si/Al molar ratio from 4 to 8.5;
zeolites β having an Si/Al molar ratio greater than 8, generally between 10 and 100, preferably between 12 and 50, and more preferably still between 12 and 35;
titanium-containing zeolites β having an Si/Al ratio greater than 50, preferably between 200 and 600 and the Ti content expressed in % by weight of $TiO_2$ varies between 0.1 and 10%, preferably between 1 and 5%;
titanium-containing zeolites β with no aluminium or with a very low aluminium content (Si/Al ratio greater than 100 000); the Ti content expressed in % by weight of $TiO_2$ varies between 0.1 and 10%, preferably between 1 and 5%, for example TiBEA;
zeolites Y, in particular zeolites obtained after dealumination treatment (for example hydrotreatment, washing with the aid of hydrochloric acid or treatment with silicon tetrachloride) and mention may more particularly be made of zeolites US-Y having an Si/Al molar ratio greater than 2, preferably between 6 and 60;
zeolite X of faujasite type having an Si/Al molar ratio from 0.7 to 1.5,
zeolites ZSM-5 or aluminium silicalite having an Si/Al molar ratio from 10 to 500;
zeolite ZSM-11 having an Si/Al molar ratio from 5 to 30;
mesoporous materials of MCM type, more particularly MCM-49 and MCM-41 having an Si/Al molar ratio between 10 and 100, preferably, between 15 and 40;
microporous materials, for example MCM-22.

Among all these zeolites, for the process according to the invention, use is preferably made of zeolites β and Y, in particular zeolites β.

Irrespective of the nature of the zeolite, it may be necessary, in order to obtain the desired Si/Al ratio, to carry out a dealumination treatment. Thus, the methods known to a person skilled in the art may be carried out, among which mention may be made, by way of example and non-limitingly, of calcinations in the presence of vapour, calcinations in the presence of water vapour followed by attack by mineral acids ($HNO_3$, HCl, etc.), direct dealumination treatments by reactants such as silicon tetrachloride ($SiCl_4$), ammonium hexafluorosilicate (($NH_4)_2SiF_6$)), ethylenediaminetetracetic acid (EDTA) and also the monosodium or disodium form thereof. A dealumination treatment may also be carried out by direct acid attack with solutions of mineral acids such as, for example, hydrochloric acid, nitric acid and sulphuric acid or of organic acids such as, in particular, acetic acid or oxalic acid. Furthermore, any combination of the aforementioned dealumination methods is also possible.

For the process according to the invention, it is also possible to use a zeolite that has undergone an activation via calcination. The calcination operation is conducted at a temperature between 200 and 800° C., preferably between 400 and 700° C., for a duration varying from 1 to 24 hours, preferably from 5 to 8 hours. The zeolites used in the process of the invention are known products described in the literature. Zeolites that are commercially available may be used, or else they can be synthesized according to the processes described in the literature.

The zeolite constitutes the catalytic phase of the process according to the invention. It may be used alone or as a mixture with a mineral matrix. According to the invention, the term "catalyst" will denote the catalyst made entirely from zeolite or from a mixture with a matrix prepared according to techniques known to a person skilled in the art. For this purpose, the matrix may be selected from metal oxides, such as aluminium, silicon and/or zirconium oxides, or else from clays and more particularly kaolin, talc or montmorillonite.

In the catalyst, the content of the active phase represents from 5 to 100% of the weight of the catalyst.

The catalysts may be in various forms in the process of the invention: powder, shaped products such as granules, for example extruded granules, or beads or pellets, which are obtained by extrusion, moulding, pressing or any other known process type. In practice, on an industrial scale, it is the granule or bead forms which offer most advantages both from the viewpoint of effectiveness and from the viewpoint of convenience in use.

Advantageously, the process according to the invention is athermic and therefore releases no or very little heat, enabling a particularly easy control of the reaction and of the heating conditions. Thus, for the process according to the invention, the reaction temperature may be between 30 and 120° C., preferably between 40 and 90° C.

For the process according to the invention, the pressure is generally autogenous and may advantageously be maintained below 10 bar.

Particularly advantageously, the process according to the invention is carried out in the absence of a source of hydrogen and with no particular solvent.

The process according to the invention may be carried out in the liquid phase. The liquid phase is advantageous since the reaction is then generally very selective and may reach or exceed 96% selectivity.

Particularly advantageously, the invention relates to a process (P) for preparing cyclohexanone and isopropanol by transfer of a hydride from cyclohexanol to acetone in a cyclohexanol/acetone molar ratio ranging from 1/10 to 2/1, preferably ranging from 1/8 to 1/2, and in the presence of a heterogeneous catalyst.

The preferences of the conditions for implementing the process according to the invention also relate to the process (P) according to the invention.

For the process according to the invention, the reaction may be carried out in continuous mode or in batch mode. The reaction technology may be a perfectly-stirred reactor with a catalyst in suspension but also a fixed bed to which a portion of the stream is recycled to more easily control the conversion. The streams supplied should generally have a minimal water content, advantageously of less than 1% by weight, so as not to degrade the performances of the reaction with certain catalysts.

The invention also relates to a mixture of compounds useful for implementing the process according to the invention. Thus, the invention also relates to a mixture comprising a ketone of formula (I), an alcohol of formula (II), an alcohol of formula (III) and a ketone of formula (IV),

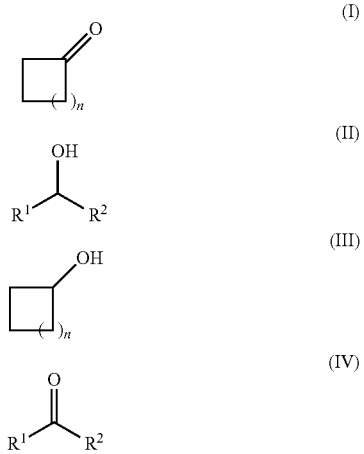

in which:
n represents an integer ranging from 1 to 9;
$R^1$ and $R^2$ independently represent a $C_1$-$C_{10}$ hydrocarbon-based group.

For the mixture according to the invention, n advantageously represents 2, 3, 4, 5 or 9, in particular 2, 3 or 9. Preferably, n represents 3.

Preferably, for the mixture according to the invention, $R^1$ or $R^2$ independently represent $CH_2R^3$, $CHR^4R^5$ or $CR^6R^7R^8$, in which:

$R^3$ represents a linear or branched $C_1$-$C_9$ alkyl;
$R^4$ and $R^5$ independently represent a linear or branched $C_1$-$C_8$ alkyl;
$R^6$, $R^7$, $R^8$ independently represent a linear or branched $C_1$-$C_6$ alkyl.

Most preferably, $R^1$ and $R^2$ independently represent methyl, ethyl, n-propyl, iso-propyl, t-butyl; most particularly, $R^1$ and $R^2$ represent methyl.

Thus, the ketone of formula (IV) is advantageously selected from low molecular weight ketones, in particular from ketones for which the molecular weight is less than 130 g/mol, or even less than 100 g/mol.

Within the mixture according to the invention, the compounds of formulae (I) to (IV) may be present in a wide ratio range. Advantageously, the alcohol of formula (III) and the ketone of formula (IV) are present in a (III)/(IV), alcohol of formula (III)/ketone of formula (IV), molar ratio ranging from 1/10 to 2/1. For the mixture according to the invention, the (III)/(IV) ratio is advantageously selected between 1/8 and 1/2.

As an example of a particularly advantageous mixture according to the invention, mention may be made of the acetone, cyclohexanol, isopropanol and cyclohexanone mixture, in particular such a mixture for which the cyclohexanol/acetone molar ratio ranges from 1/10 to 2/1, preferably from 1/8 to 1/2.

The following example illustrates the process of the invention, in particular the advantages of this process.

EXAMPLE 1

Into a 250 ml reactor that can operate under pressure, 100 g of cyclohexanol, i.e. 1 mol, and 175 g of acetone, i.e. 3 mol, are introduced. The mixture is stirred and 20 g of catalyst are added. The reactor is then heated at 75° C. and at autogenous pressure, and kept under these conditions for 3 hours. The reaction medium is then analysed by gas chromatography (GC). The results obtained are presented in Table 1.

TABLE 1

| catalyst | Degree of conversion % Cyclohexanol | Yield % Cyclohexanone |
|---|---|---|
| Zeolite HBEA (Si/Al = 12.5) Zeolyst | 15 | 14 |
| Zeolite HBEA (Si/Al = 12.4) Sud Chemie | 15 | 12 |

The feasibility of the reaction is demonstrated and the selectivity is greater than or equal to 80%.

EXAMPLE 2

Into a reactor that can operate under pressure, 100 g of cyclohexanol, i.e. 1 mol, and 350 g of acetone, i.e. 6 mol, are introduced. The mixture is stirred and 20 g of catalyst are added. The reaction medium is then heated at 75° C. and at autogenous pressure, and kept under these conditions for 3 h. The reaction medium is then analysed by GC. The results obtained are listed in Table 2.

TABLE 2

| catalyst | Degree of conversion % Cyclohexanol | Yield % Cyclohexanone |
|---|---|---|
| Zeolite HBEA zeolyst - CP 806 calcined 500° C. Si/Al = 12.5 | 43 | 42 |

For this test, the conversion is greatly improved while retaining an excellent selectivity.

The invention claimed is:

1. A process for preparing a ketone of formula (I) and an alcohol of formula (II):

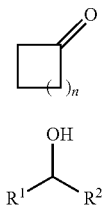

(I)

(II)

the process comprising transferring a hydride, in the presence of a heterogeneous catalyst, between an alcohol of formula (III) and a ketone of formula (IV), present in a (III)/(IV), alcohol of formula (III)/ketone of formula (IV), molar ratio ranging from 1/8 to 1/2, said catalyst being selected from the group consisting of a zeolite, a hydroxyapatite with a Ca/P atomic ratio, a tricalcium phosphate, a magnesium phosphate, an olivine, an alumina and a rare-earth oxide, alone or as a mixture with other oxides,

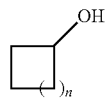

(III)

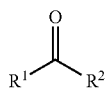

(IV)

in which:

n represents an integer ranging from 1 to 9; and
$R^1$ and $R^2$ independently represent a $C_1$-$C_{10}$ hydrocarbon-based group.

2. The process as defined by claim 1, wherein n represents 2, 3, 4, 5 or 9.

3. The process as defined by claim 1, wherein $R^1$ or $R^2$ independently represent $CH_2R^3$, $CHR^4R^5$ or $CR^6R^7R^8$, in which:

$R^3$ represents a linear or branched $C_1$-$C_9$ alkyl;
$R^4$ and $R^5$ independently represent a linear or branched $C_1$-$C_8$ alkyl; and
$R^6$, $R^7$, $R^8$ independently represent a linear or branched $C_1$-$C_6$ alkyl.

4. The process as defined by claim 1, wherein the ketone of formula (IV) is a low molecular weight ketone having a molecular weight that is less than 130 g/mol.

5. The process as defined by claim 1, wherein the reaction temperature is from 30° C. to 120° C.

* * * * *